United States Patent
Atchison (10) Patent No.: US 10,161,836 B2
(45) Date of Patent: Dec. 25, 2018

(54) PIPELINE SAMPLING SYSTEM AND METHOD

(71) Applicant: Martin Atchison, Manvel, TX (US)

(72) Inventor: Martin Atchison, Manvel, TX (US)

(*) Notice: Subject to any disclaimer, the term of this patent is extended or adjusted under 35 U.S.C. 154(b) by 567 days.

(21) Appl. No.: 14/809,728

(22) Filed: Jul. 27, 2015

(65) Prior Publication Data

US 2015/0330873 A1 Nov. 19, 2015

Related U.S. Application Data

(63) Continuation-in-part of application No. 14/282,433, filed on May 20, 2014, and a continuation-in-part of application No. 14/282,342, filed on May 20, 2014, and a continuation-in-part of application No. 14/187,901, filed on Feb. 24, 2014, now Pat. No. 9,562,839, said application No. 14/282,342 is a continuation of application No. 14/187,901, filed on Feb. 24, 2014, now Pat. No. 9,562,839, said application No. 14/282,433 is a continuation of application No. 14/187,901, filed on Feb. 24, 2014, now Pat. No. 9,562,839.

(60) Provisional application No. 62/034,345, filed on Aug. 7, 2014, provisional application No. 61/769,896, filed on Feb. 27, 2013.

(51) Int. Cl.
*G01N 1/20* (2006.01)
*G01N 9/36* (2006.01)
*G01N 1/16* (2006.01)

(52) U.S. Cl.
CPC ............ *G01N 1/20* (2013.01); *G01N 1/2035* (2013.01); *G01N 9/36* (2013.01); *G01N 1/16* (2013.01); *Y10T 29/49828* (2015.01); *Y10T 137/0402* (2015.04); *Y10T 137/598* (2015.04)

(58) Field of Classification Search
CPC .. G01N 1/10; G01N 1/16; G01N 1/20; G01N 1/2035; G01N 2001/205; G01N 2001/2057; G01N 2001/2064; G01N 2001/2071
USPC .................. 73/32 R, 863.71, 864.63, 864.73
See application file for complete search history.

(56) References Cited

U.S. PATENT DOCUMENTS

| | | | | |
|---|---|---|---|---|
| 3,282,113 | A | * 11/1966 | Sachnik | F16L 55/00 73/863.02 |
| 4,307,620 | A | 12/1981 | Jiskoot | |
| 4,346,609 | A | * 8/1982 | Diesel | G01N 1/2035 73/863.33 |
| 4,413,533 | A | * 11/1983 | Diesel | G01N 1/2035 73/863.31 |
| 4,494,413 | A | * 1/1985 | Bukkems | G01N 1/2035 366/137 |
| 4,712,434 | A | * 12/1987 | Herwig | G01N 1/2035 73/863.71 |

(Continued)

*Primary Examiner* — Daniel S Larkin
(74) *Attorney, Agent, or Firm* — Kenneth L. Nash; Thomas D. Nash (57) ABSTRACT

The present invention describes a sampling system and densitometer system for sampling fluids from a pipeline. A flow loop is set up which continuously collects fluid from the pipeline and then returns the fluid with a minimum fluid flow rate so that the fluid is representative of fluid flowing through the pipeline at the time of sampling. For each sample, pressurized fluid is taken from the flow loop and directed to a pressurized sampling chamber. The sample is then directed by gravity to a removable sample container, which may be pressurized or unpressurized, in each sampling cycle.

17 Claims, 3 Drawing Sheets

(56) References Cited

U.S. PATENT DOCUMENTS

| | | |
|---|---|---|
| 5,098,563 A | 3/1992 | Xin-Shen |
| 6,196,051 B1 | 3/2001 | Marshall et al. |
| 6,208,913 B1 | 3/2001 | Marshall et al. |
| 6,742,404 B2 * | 6/2004 | Smith ............... G01N 1/14 73/863.03 |
| 8,347,694 B2 | 1/2013 | Welker et al. |
| 8,424,397 B2 | 4/2013 | Fjerdingstad |
| 8,429,950 B2 | 4/2013 | Wright |
| 8,499,613 B2 | 8/2013 | Ziglioli et al. |
| 2008/0098829 A1 | 5/2008 | Nathan |

\* cited by examiner

PIPELINE SAMPLING SYSTEM AND METHOD

This application claims the benefit of U.S. Provisional Patent Application No. 62/034,345 filed Aug. 7, 2014. This application is a continuation in part of U.S. patent application Ser. No. 14/282,342 filed May 20, 2014, and is a continuation in part of U.S. patent application Ser. No. 14/282,433 filed May 20, 2014, and is a continuation in part of U.S. patent application Ser. No. 14/187,901 filed Feb. 24, 2014, now U.S. Pat. No. 9,562,839. U.S. patent application Ser. No. 14/282,342 filed May 20, 2014 and U.S. patent application Ser. No. 14/282,433 filed May 20, 2014, are both continuing applications of U.S. patent application Ser. No. 14/187,901 filed Feb. 24, 2014, now U.S. Pat. No. 9,562,839, which claims the benefit of U.S. Provisional Patent Application No. 61/769,896 filed Feb. 27, 2013. The above applications are each incorporated herein by reference.

BACKGROUND OF THE INVENTION

Field of the Invention

The present invention relates generally to sampling systems for pipelines and, more specifically, in one or more embodiments, to a sampling system that automatically produces pressurized or unpressurized samples from a pressurized pipeline.

Background of the Invention

Sampling systems have been utilized for decades to monitor the density of the fluids in pipelines and the type and quality of the liquid hydrocarbons flowing therethrough. Accurate density readings and samples of the hydrocarbons are important for both the pipeline companies and the users of the pipelines desire to obtain the most accurate readings for efficient product processing. Given the volume of the hydrocarbons and the cost, the results affect the significant costs involved for the parties involved in transport of the hydrocarbons through the pipeline.

Those of skill in the art have long sought a better sampling system to provide more accurate readings in a more effective manner. Consequently, those of skill in the art will appreciate the present invention, which addresses the above and/or other problems.

SUMMARY OF THE INVENTION

Accordingly, it is an object of the present invention to provide an improved sampling system.

Another possible object of the invention is a sampling system that provides automated sampling of pressurized fluid in the pipeline.

Yet another object of the invention is to provide a sampling system that produces pressurized or unpressurized samples to be tested.

A further object of the present invention is to provide an improved system operable to program the number of samples needed in accord with desired sampling characteristics including size of sampling containers, batch size, and the like, to produce multiple pressurized or unpressurized samples.

Accordingly, the present invention provides a method for a sampling system for taking samples from a pipeline comprising providing a sample line connectable to the pipeline for circulating pressurized fluid from the pipeline and through the sample line whereupon the pressurized fluid is returned to the pipeline.

A processor is programmed for operating at least one valve to allow fluid flow from the sample line to a sampling chamber and then closing the at least one valve with respect to the sample line.

The processor is additionally programmed for operating the at least one valve to provide a flow path from the sampling chamber to a removable sample container. The sampling chamber is connected to a sample discharge mechanism so that when the at least one valve provides the flow path to the removable sample chamber and the at least one valve is closed with respect to the sample line, then the sample discharge mechanism is operable to urge a respective sample into the removable sample container.

In one embodiment, a method for making a sampling system for taking samples from a pipeline, may comprise steps such as providing a sample line connectable to the pipeline for circulating pressurized fluid from the pipeline and through the sample line whereupon the pressurized fluid is returned to the pipeline, providing a processor programmed for operating at least one valve to allow fluid flow from the sample line to a sampling chamber and then closing the at least one valve with respect to the sample line, and providing the processor is programmed for operating the at least one valve to provide a flow path from the sampling chamber to a removable sample container. Other steps may comprises providing that the sampling chamber is connected to a sample discharge mechanism so that when the at least one valve provides the flow path to the removable sample chamber and the at least one valve is closed with respect to the sample line, then the sample discharge mechanism is operable to urge a respective sample into the removable sample container.

The method may comprise providing that the sampling chamber is mounted above the removable sample container whereby the sample discharge mechanism utilizes gravity and/or differential pressure to induce flow from the sampling chamber to the removable sample container.

The method may comprise providing that the sample discharge mechanism comprises a check valve for the connection of the sampling chamber to ambient air so that when ambient air is connected to the sampling chamber then gravity urges a respective sample into the removable sample container.

The method may comprise providing that the sample discharge mechanism comprises at least one of a check valve or a piston to urge the respective sample into the removable sample container.

The method may comprise providing that the processor is programmed to perform one or more sample chamber purging cycles that are dumped to a purge outlet prior to allowing the fluid to drain into the removable sample container.

The method may further comprise providing that the removable sample container is unpressurized but the sample container could also be pressurized.

The method may further comprise providing that the processor is programmed to control a plurality of valves for directing the samples to a plurality of removable sample containers.

The method may comprise programming the processor to determine how many of the samples to take and when to take the samples for each of the plurality of removable sample containers based on variables that may comprise a batch size, or a container size, or the like.

The method may further comprise providing that the at least one valve comprises a first valve operatively connected to the sample line and the sampling chamber, and a second valve operatively connected to the sampling chamber and the removable sample container. Other steps may comprise providing that the sample discharge mechanism comprises a third valve connected to provide selective communication with ambient air and the sampling chamber so that when the third valve is open then gravity flow urges the respective sample to drain from the sampling chamber into the removable sample container.

In another embodiment, a sampling system for taking samples from a pipeline may comprise a sample line with an input connection and an output connection. The sample line is operable for connection to the pipeline to receive pressurized fluid to be sampled from the pipeline and for returning the pressurized fluid to the pipeline.

Other elements may comprise a sampling chamber, a removable sample container and at least one valve operatively connected to the sample line, the sampling chamber, and the removable sample container.

A sample discharge mechanism is connected to the sampling chamber to urge a respective sample from the sampling chamber to the removable sample container by gravity, calibrated piston, differential pressure, or the like.

A processor is operatively connected to the at least one valve to control fluid communication between the sample line and the sampling chamber and to control fluid communication between the sampling chamber and the removable sample container.

In one possible embodiment, the at least one valve comprises a first valve operatively connected to the sample line and the sampling chamber, and a second valve operatively connected to the sampling chamber and the removable sample container.

In one possible embodiment, the sample discharge mechanism further comprises a third valve connected to provide selective communication with ambient air and the sampling chamber so that when the third valve is open then gravity flow urges the respective sample to drain from the sampling chamber into the removable sample container.

The sampling system may further comprise the processor programmed to perform one or more sample chamber purging cycles that are dumped to a purge outlet prior to allowing the respective sample to drain into the removable sample container.

The sampling system may further comprise the at least one valve being connected to the purge outlet.

The sampling system may further comprise a plurality of valves in fluid communication with the sample line, a plurality of sampling chambers, and a plurality of removable sample containers. The processor is operatively connected to the plurality of valves to sequentially operate the plurality of valves to fill the plurality of removable sample containers.

The sampling system may further comprise the removable sample container being unpressurized or pressurized.

The sampling system may further comprise a pump that turns on only when a flow rate through the sample line is below a predetermined flow rate.

The sampling system may further comprise a densitometer.

In one embodiment, the processor is operable to adjust a number of samples to take in relationship to a size of the removable sample container and/or a batch size.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE INVENTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
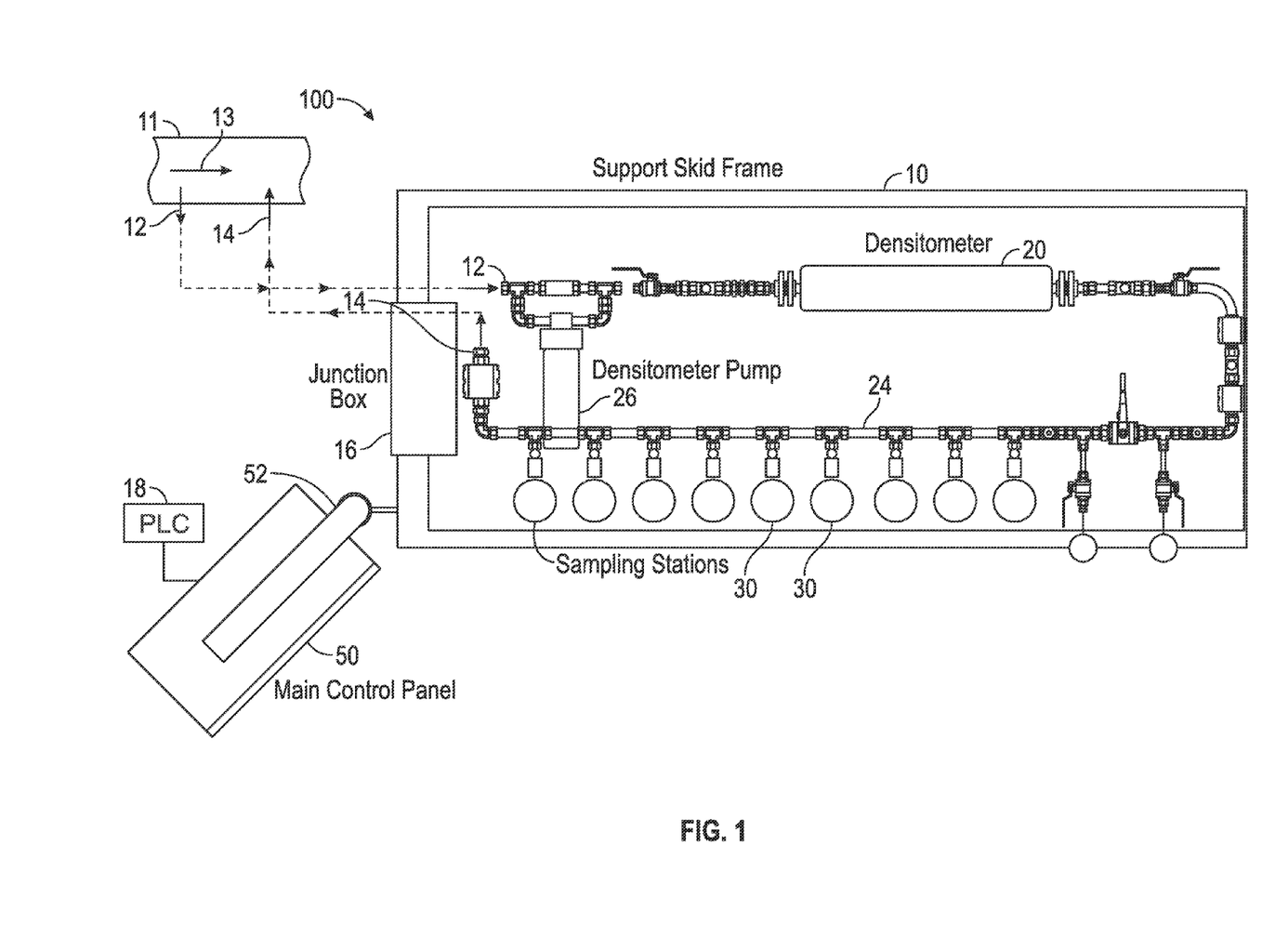
FIG. 1 is a top view of a sampling system and densitometer skid in accord with one possible embodiment of the present invention.

Looking to FIG. 1, a top view of sampling system and densitometer skid 100 in accord with one possible embodiment of the present invention is depicted. Sampling system 100 has multiple sampling stations 30 that connect to pressurized sample line 24. In one preferred embodiment, sampling system 100 utilizes nine independent sampling stations 30 to provide automated sampling of pipeline fluids at different times and/or batches.

Input 12 connects to pipeline 11 and supplies pressurized sample line or loop 24 with a continuous supply of pipeline fluid 13 that is returned back to pipeline 11 from output 14. Sample line or loop 24 provides a loop of pressurized fluid 13 that may continuously flow from and returns to the pipeline. The speed of fluid flow through sample line or loop 24 is monitored and controlled if necessary to provide a minimum flow rate. Accordingly, fluid in pressurized sample line 24 is representative of fluid 13 flowing through pipeline 11 at any particular time. In a preferred embodiment, scoops utilized in the parent applications to this application can normally be utilized to maintain fluid flow through sample line 24 without the need for a pump although as described herein a pump may be utilized to maintain a minimum flow rate.

The sample stations 30 are automatically controlled by main control panel 50 and more specifically programmable logic controller (PLC) 18 which operates the actuators and valves associated with each sample station. Sampling stations 30 are utilized to sample pipeline fluid 13 whereupon PLC 18 records the time and other information so that the samples provide a reliable record of the pipeline fluid 13. This information is important to determine the values and costs to the pipeline fluid owners and the pipeline owners.

In one possible embodiment, sampling system and densitometer skid 100 is broadly segmented into three different sections. First, a densitometer system, second a sampling system, and third, a safety & emergency control. Programmable logic controller 18 is used to control the different aspects of the three sections system 100. In one embodiment, controller 18 can be installed in a main control room for the pipeline and controlled by the off-site command center via independent link. In another embodiment, controller or PLC 18 will be incorporated into control panel 50, which may be connected directly to skid frame 10 by control panel arm 52. Skid 100 may be located at the desired location adjacent the pipeline where sampling of pipeline fluid 13 is to take place.

Fluid flow from the pipeline is normally directed to densitometer 20 where the density is monitored directly by a computer, and in a preferred embodiment, an Omni Flow computer (Not depicted). This computer can be wired to densitometer 20 by the site personnel or an approved vendor. Densitometer 20 will measure the density of the fluids passing through sampling system 100, and more specifically sample line 24.

Pump 26 is powered by skid power junction box 16 providing 110 VAC. Densitometer pump 26 can be controlled by PLC 18 which monitors an in-line flow turbine meter, which can be mounted in sample line 24, and determines from set parameters whether pump 26 needs to be on or off. It is desirable that the flow rate of fluid be maintained with at least a minimum flow rate so that fluid in the loop is representative of fluid in the pipeline. In one embodiment, if PLC 18 registers a parameter of 3 GPM (gallons per minute) or greater, then pump 26 does not need to be on; if less than 3 GPM, pump 26 is engaged. In one embodiment, the turbine meter may be located near system inlet 12 or outlet 14 of system skid 100. Pump 26 is magnetically coupled to the gear pump head and will disengage when dead-headed or over pressured. A free spin of the pump motor will be captured by PLC 18 to determine the re-set of the pump, i.e., turn off to complete stop, then back on again to re-engage the coupler. Pump 26 is designed as a "booster" pump for system 100, but will be able to function in 100% duty cycle at a rate of no greater than 8 GPMS.

Both pump 26 and the turbine can be located "upstream" of densitometer 20 and in a preferred embodiment, pump 26 has a surge tank/accumulator with floating piston to off-set any pressure of flow surge due to the start up or shut-down of pump 26. Pump 26 can be located upstream to eliminate the pressure drop due to the close proximity of pump 26 to densitometer 20.

Figure 2:
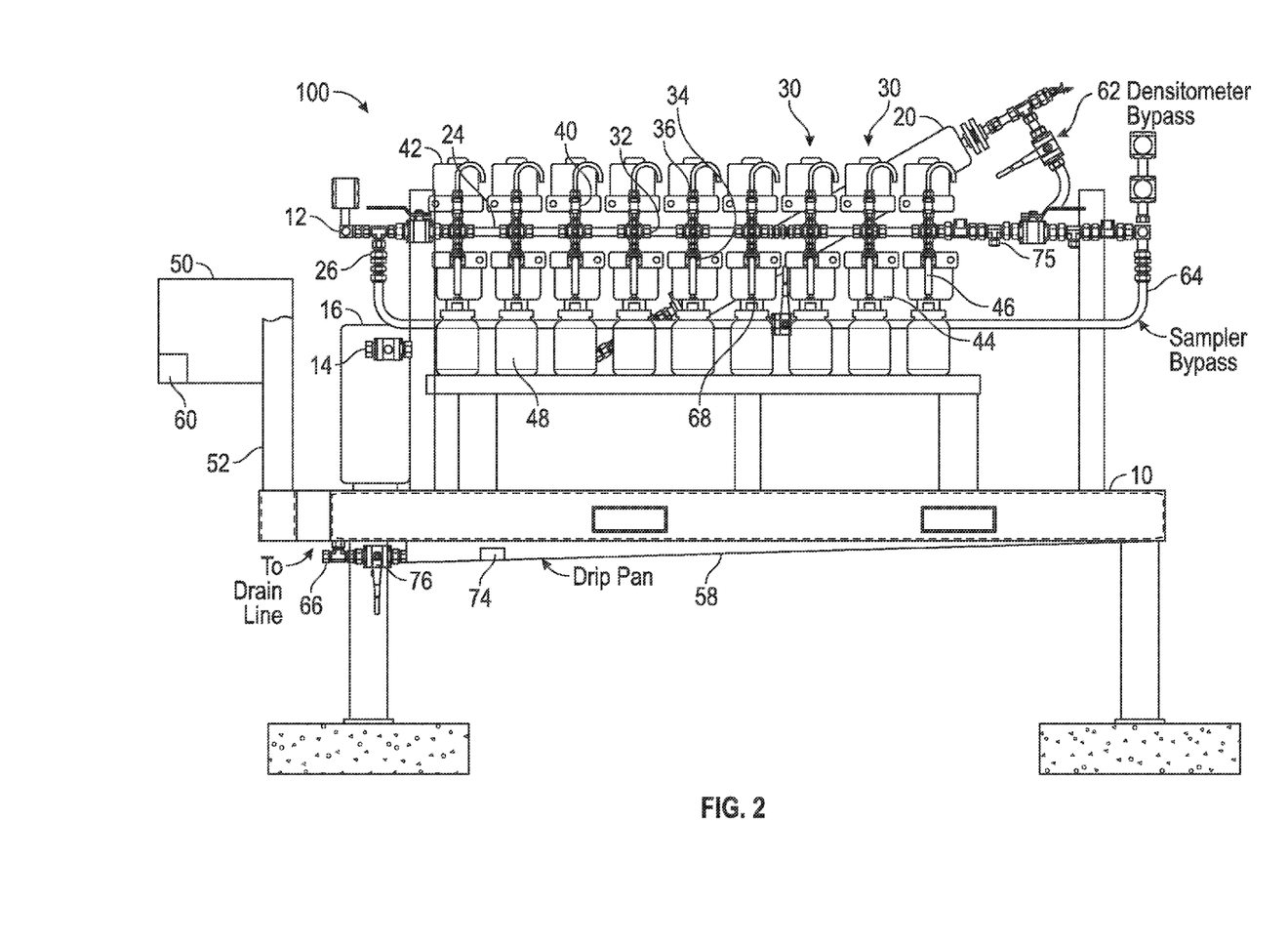
FIG. 2 is a side elevational view of a sampling system and densitometer skid in accord with one possible embodiment of the present invention.

Turning now to FIG. 2, a side elevational view of sampling system and densitometer skid 100 is depicted in accord with one possible embodiment of the present invention. FIG. 2 shows the nine sampling stations 30 that were also shown in FIG. 1. The equipment for each sampling station can be identical or essentially identical although each sampling station may operate at different times to collect different samples. Even though typically operated at different times, the general operation of any individual sample station applies to all of the sampling stations.

Figure 3:
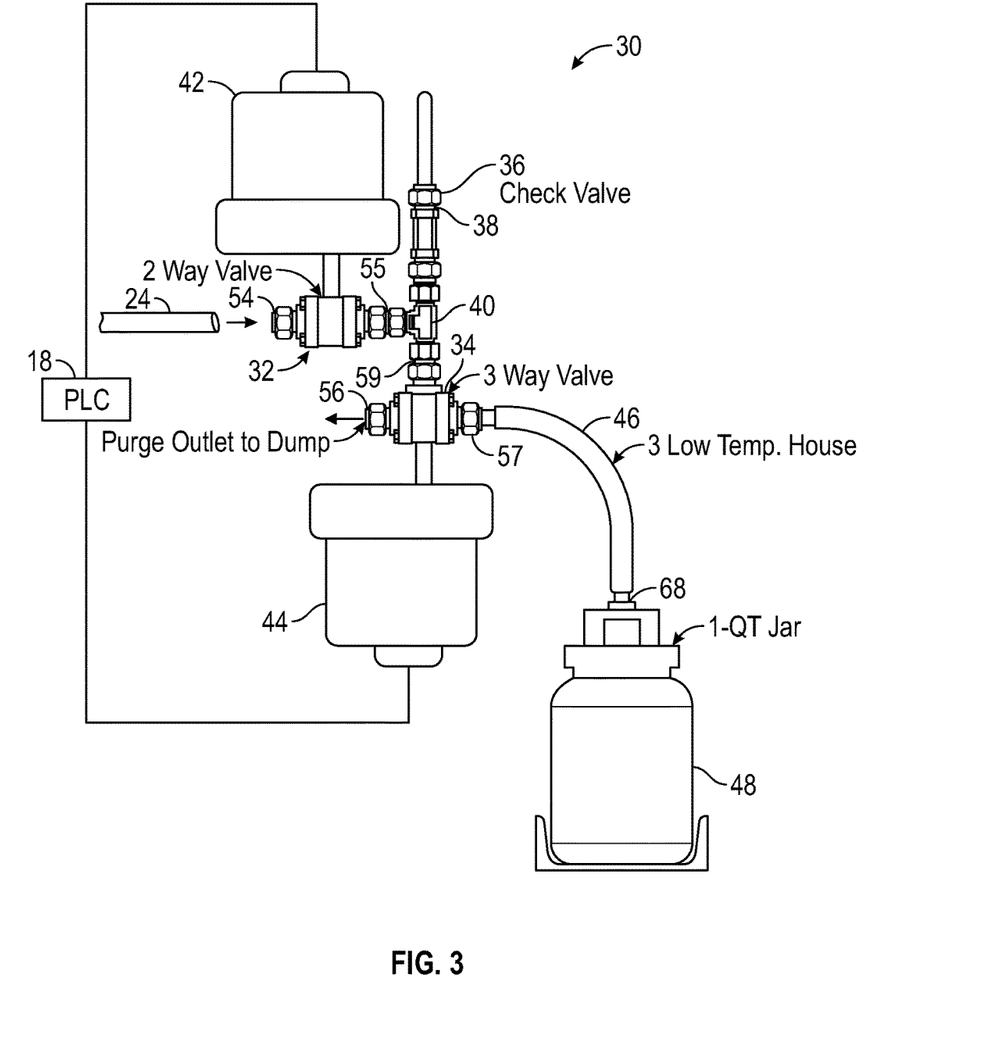
FIG. 3 is an elevational view of a sampling station in accord with one possible embodiment of the present invention.

Accordingly, sampling system 100 has multiple sampling stations 30, such as that shown in FIG. 3, each of which may typically accumulate multiple individual samples into respective removable sample containers 48 as discussed in more detail herein. In one possible example of operation, forty to sixty samples could be taken during pipeline operation and stored in each container 48 to provide a representative sample of pipeline fluid during a time period of operation of the pipeline. In one possible embodiment, six stations are designated for gasoline and three stations for diesel. The samples taken may be pressurized or unpressurized as desired.

As discussed herein, fluid flow from the pipeline is normally directed to densitometer 20 where the density is monitored directly by a computer before passing through pressurized line 24. Sampling system 100 also provides densitometer bypass 62 and sampler bypass 64 for situations in which sampling is not desired, but is still advantageous for skid 100 to be connected to pipeline 11.

Sampling stations 30 can be attached to sampling containers 48 by "Clif Mock" sampling fitting & screw-on lids. Fitting 68 contains an adjustable overfill/over pressure valve which prevents container 48 from being pressurized or over filled by an uncontrolled sample sequence or mechanical failure of system 100.

Referring to FIG. 2 and FIG. 3, the sampling begins by activating two-way valve 32 (shown enlarged in FIG. 3) allowing sampling chamber 40 to be filled while still under pressure with hydrocarbon fluids from sample line 24 through inlet 54 (See FIG. 3). Sampling chamber 40 may comprise the tubing between two-way valve 32, sample discharge mechanism 36 which comprises a check valve, and three-way valve 34. However, other arrangements of valves may be utilized. A multiport valve could be utilized to replace valves 32 and 34. A check valve for sample discharge mechanism 36 may be replaced by other types of sample discharge mechanisms as discussed herein. If purging is not required to reduce the possibility of cross contamination between samples, then valve 32 could be eliminated requiring only valve 34.

In one possible non-limiting embodiment, sampling chamber 40 comprises a vertical portion of tubing and is mounted above container 48 whereby gravity flow is encouraged. Two-way valve 32 opens to capture a sample in sampling chamber 40. Once two-way valve 32 is closed, then using three-way valve 34 and sample discharge mechanism 36, which may comprise a check valve open to ambient air to connect with sampling chamber 40, the fluid captured in sampling chamber 40 is dumped by gravity flow into container 48. In this embodiment, sample discharge mechanism 36 is a one-way valve that opens to ambient air after valve 34 is opened to allow gravity flow of fluid from sampling chamber 40 into container 48. Check valve 36 otherwise seals off the top end of sampling chamber 40. Thus, sampling chamber 40 is under pressure until three-way valve 34 opens.

In one possible embodiment, valve 34 is a three-way valve. In this embodiment, valve 34 provides two outlets for fluid to selectively flow either to container 48 or a purge outlet. As well, three-way valve 34 may have a closed position to prevent flow through valve 34 from sampling chamber 40. Accordingly, valve 34 allows for fluid purging at the beginning of a sampling batch to reduce contamination from previous samples.

In operation, two-way valve 32 will be opened and shut allowing the capture of fluid in sampling chamber 40. Then three-way valve 34 opens and one-way valve 36 opens allowing the fluid to be released to drain line outlet 56 which connects to drip pan 58. In one embodiment, this purge cycle occurs twice or any desired number of times to cleanse or purge sampling chamber 40 of old product residual. Once the purging cycle is accomplished to provide clean uncontaminated samples, the sampling cycle may begin.

The frequency of the sampling will be calculated by PLC 18 based upon factors including, but not limited to, the batch size, the meter tube/system volume, which sets the number of cycles for one quart capacity, and the barrel count from the existing metering skid. PLC 18 is also operable to adjust the number of samples to take in relationship to the size of removable sample containers 48 and the batch size. The sampling will take place within the middle 90% of the batch, allowing for the purge cycle at the beginning and a finish sampling without capturing any interface fluid. In a preferred embodiment, the total amount of the sample in container 48 is approximately one quart per station, which is cumulative of approximately forty to sixty samples from the sampling chamber 48. The amount of the batch will be input into PLC 18 so that at the end of the appropriate total flow count, the next sampling may begin. At the end of the batch, PLC 18 will send a print signal to the label printer to print out the sample container 48 number, date, time, and any other pertinent information that is given to PLC 18 from the control center.

Sampling from each sampling station 30 may typically continue in sequence from the first container 48 through the sixth container 48 for gasoline and for the seventh through ninth container 48 for diesel. This sequence can be mixed but preferably proceeds in numerical order of each segment. Once a container 48 has been filled and another batch is started, PLC 18 will take that container 48 location "off-line" until the respective sampling system 30 has been reset at skid 100. In one embodiment, for each container 48 location an indicator light indicates the status of the container, such as a full container waiting to be replaced. A reset green lighted button may be used to clear the use of that location again by PLC 18 once a new empty container 48 is put in place of the newly filled one. The filled container 48 will be disconnected, which may be accomplished manually be a user in this embodiment, labeled with the label printed out by PLC 18, and stored in the on-site storage cabinet or other suitable storage area. There is an "emergency sample port" 75 for sampling when the skid is completely offline, which may be used to allow manual sampling.

An emergency system will include the monitoring of any leaks that pose a threat to skid system 100 and the surroundings or any associated personnel. Drip pan 58 is installed under skid 10 to catch any drips, spills, leaks, and purge samples. Drip pan 58 will have level switch 74 which, when engaged and indicating a large amount of leakage, will activate the closure of main inlet 12 and outlet 14 to system 100. Emergency Off/Auto/Manual switch 60 can be located on control panel 50. This will also send a signal to PLC 18 which will activate warning(s) for the personnel on site and/or off-site personnel. Existing air monitoring devices at each location will detect any fumes or vaporized liquids that have missed detection by system 100. Manual valve 76 (See FIG. 2) is installed for the draining of drip-pan 58 into main drain line 66. Valve 76 will normally be closed to prevent any back pressure fumes from entering the skid area. A high pressure safety valve (PSV) will be installed in the main line of skid system 100 to protect the pressure rating of the pipeline from sampling pump 26. This will be connected to the skid drain line which is connected down-stream of the drip-pan valve 76.

It is noted that sampling containers 48 can be glass two quart jars with plastic lids. However containers 48 may comprise other suitable materials of various sizes for samples. These containers will be recycled through the normal waste disposal system once the contents have been discarded and containers 48 are allowed to "dry" of any sampling fluids. The disposal of the contents of containers 48 will be performed on site at the local "dumping funnel" and allowed to dry on skid 10 over drip pan 58.

Looking now to FIG. 3, an elevational view of a non-limiting example of single sampling station 30 from sampling system skid 100 is depicted. Line 24 connects to inlet 54 of sampling station 30 as shown in FIG. 1 and FIG. 2, where two-way valve 32 controls flow into sampling chamber 40. In a preferred embodiment, two-way valve 32 is a Swagelok valve model "SS-63TS8". The sample proceeds through inlet port 54, then through valve 32 when valve 32 is opened by actuator 42, and out though single outlet port 55. In this embodiment, two-way valve 32 may be a rotary valve which can be configured to be open with the rotary element at 0 degrees and closed at 90 degrees. In this case, the "90" degree position is a normally closed position with "0" denoting that port 54 and port 55 are open to each other to allow flow of pressurized fluid into sampling chamber 40.

Two-way valve 32 is in a normally closed position when any station 30 is not in use. In one embodiment, actuator 42, which operates valve 32, may comprise two cams and switches (not shown) that provide travel and location status of valve 32 to PLC 18. In this embodiment, PLC 18 controls valve 32 and valve 34. When sampling station 30 is active, two-way valve 32 will be repeatedly opened and shut allowing the capture of multiple samples of fluid in the sample chamber 40.

In one possible embodiment, from the closed position (90 deg), 120 VAC power from PLC 18, which may connect to valve actuator 42 through a relay or the like, is operably connected to valve actuator 42. Valve actuator 42 is operable to rotate the valve element to open and close the valve, in this embodiment a 90 degree rotation. Although only the valve element is rotated, for convenience herein it is stated that the valve is rotated. Valve 32 will rotate counter clockwise 90 degrees to the open the valve (0 deg. position). The rotation will stop when the cam trips the switch at the zero degree position and disconnects the motor power. The travel cam, powered from PLC 18, will then indicate that the valve is at the open position by connecting the power signal back to PLC 18. PLC 18 will then power actuator 42 to rotate valve 32 clockwise 90 degrees back to the closed position (90 deg.) where the cam will trip a switch at 90 degrees stopping it there. The travel cam, powered from PLC 18, will then indicate that the valve is at the closed position. Other types of sensors could be used to indicate open/closed position of each valve. This sample cycle will be performed some forty to sixty times to reach an 85% fill of the sample container 48. For each sample cycle, sample chamber 40 is filled and then emptied into sample container 48.

In one embodiment, sample discharge mechanism 36 which may comprise a check valve that can be used to trigger PLC 18 to use actuator 42 to energize to the closed position of two-way valve 32 once sensor or switch 38 is triggered to indicate a pressurized sample has been stored in sample chamber 40. Sample discharge mechanism 36 which in this non-limiting example comprises a check valve is connected to ambient air on one end and to sampling chamber 40 on an opposite end. Sample discharge mechanism/check valve 36 is a one-way valve. Accordingly, sample discharge mechanism/check valve 36 holds pressure in sampling chamber 40 when valve 32 is open and sampling chamber 40 is pressurized. Sampling chamber 40 remains pressurized when two-way valve 32 closes while valve 34 is closed. However, the check valve opens to ambient air when three-way valve 34 opens to release the pressure in the sampling chamber 40 and allow gravity draining of fluid from sampling chamber 40 into sample container 48 or to the purge outlet. Sample discharge mechanism 36 could be another actuator operated two-way valve but in this embodiment is more conveniently a check valve that operates without the need for an another actuator control by PLC 18.

In one embodiment, three-way valve 34 is a Swagelok "SS-63XTS8" which has three openings or ports. Inlet port 59 feeds two outlet ports which are located 180 degrees apart. Either port may be opened with respect to inlet port 59 or all ports may be closed off with respect to each other in a closed position utilizing PLC 18 control of actuator 44. To better understand the working sequence the rotary element locations will be given degree positions of "0, 90, and 180" degrees, which will be the position of the rotary element in valve 34. The "90" degree position is normally closed where all ports are closed off so that there is no communication between any of the three ports. The "180" degree position allows communication between sampling chamber 40 and sample container 48, in other words inlet port 59 connects to sampling port 57. The "0" degree position connects inlet port 59 to purge or dump port 56. In another possible embodiment, three-way valve 34 could be replaced by two valves with one valve connecting to sample container 48 and the other to dump port 56.

Accordingly in this embodiment, valve 34 is a three-way valve which allows for purging at the beginning of a sampling batch. Valve 34 is in a normally closed position when sampling station 30 is not in use. When sampling station 30 is active, two-way valve 32 is repeatedly opened and shut allowing the capture of fluid in the metered tube section, or sampling chamber 40, as described herein.

Prior to and after samples are taken from the line in a particular sampling batch, three-way valve 34 can be operated to purge or clean sampling chamber 40 in the following sequence. From the closed position (90 deg.), 120 VAC power from PLC 18 will be sent to actuator 44 through a set of cams and switches (not shown). Valve 34 will rotate counterclockwise 90 degrees to dump port 56 (0 deg. position). The rotation will stop when the cam (not shown) trips a switch, disconnecting the motor power, and sending the power back to PLC 18 for an indication that valve 34 connects inlet 59 to dump port 56. PLC 18 will then power actuator 44 to rotate clockwise 90 degrees back to the closed position (90 deg.) where the cam will trip a switch stopping the rotary element there and sending the indication back to PLC 18.

The purging cycle involves opening and closing valves 32 and 34 to purge sampling chamber 40. The purging cycle involves opening valve 32, closing valve 32, whereupon sampling chamber 40 is pressurized with fluid from sample line 24, which connects to the pipe line 11. Sample discharge mechanism/check valve 36 opens when valve 34 is opened to the purge outlet. Sample discharge mechanism/check valve 36 closes after valve 34 closes. Sample discharge mechanism/check valve 36 remains closed due to being biased to the closed position. The purging cycle is performed twice or as often as desired and is called the purging cycle. Once the purging cycle is accomplished, the sampling cycle is to begin.

The sampling cycle involves opening valve 32 to fill sampling chamber 40, and then closing valve 32 whereby the sample is contained in sampling chamber 40 with valve 34 and sample discharge mechanism/check valve 36 both closed. Then valve 34 is opened to direct fluid from sampling chamber 40 through hose 46 into the removable sample container 48 which results in the one way sample discharge mechanism/check valve 36 opening to ambient or atmospheric pressure.

In other words, from the closed position (90 deg.), 120 VAC power from PLC 18 is sent to actuator 44. The valve element of three-way valve 34 will rotate clockwise 90 degrees to sample port 57 (180 deg. position). The rotation will stop when the cam (not shown) trips the switch (not shown), disconnecting the motor power, and sending power back to PLC 18 for an indication that valve 34 has opened sample port 57 to communicate with sampling chamber 40. The opening of valve 34 causes sample discharge mechanism/check valve 36 to open, release the pressure, and allow fluid to drain from sampling chamber 40 into container 48.

PLC 18 will then power actuator 44 to rotate counter clockwise 90 degrees back to the closed position (90 deg.) where the cam will trip a switch stopping valve 34 there and sending the indication back to PLC 18. This sample cycle will typically be performed some forty to sixty times depending upon the number of cycles needed to reach an 85% fill capacity of sample container 48. However, the number of samples for a one quart sample container or a two quart sample container will be adjusted accordingly. PLC 18 can adjust a number of samples to take in relationship to a size of the removable sample container, a batch size, and/or other desired factors.

In one embodiment, once filled, the sampling station 30 is taken off-line and an indicator light is activated to show an operator that the sample is ready to be removed. An operator can take the printed information and put it on the sample container 48, replace the container with a clean container 48, and press a switch (which may change a light) to place the station 30 online once again to be available as needed.

In summary of operation, fluid from the pipeline is directed to sample line 24 through which pipeline fluid continually flows. Accordingly, the fluid in sample line 24 is representative of what is flowing through the pipeline at that time. The densitometer reading is recorded.

Prior to beginning the sampling, purging cycles remove fluid that was in sampling chamber 40 and replaces the old fluid or residue with current fluid from the pipeline. PLC 18 controls the purging cycle by opening and closing two-way valve 32 at the sampling station of interest. Sample discharge mechanism 36, which may comprise a check valve, holds the sample under pressure after two-way valve 32 is closed. Then three-way valve 34 opens to direct the fluid to the purge outlet.

After the purging cycles are complete, the sampling cycles follow the same sequence except three-way valve 34 opens to direct the fluid from sampling chamber 40 to the removable sample container 48 to collect samples from the pipeline. In other words, two-way valve 32 is opened to fill sampling chamber 40 with pressurized fluid from sample line 24, which contains the fluid that is then flowing through the pipeline. Three way valve 34 opens whereupon sample discharge mechanism/check valve 36 also opens to release the pressure and allow the fluid in the sampling chamber to drain. Three-way valve 34 then closes to complete a first sampling cycle.

In accordance with the claims, valve 32 may be referred to as a first valve, valve 34 may be referred to as a second valve, and sample discharge mechanism 36 may be referred to as a third valve or check valve. It will be understood that other arrangements of valves and actuators may be utilized that accomplish the same functions. For example, three-way valve 34 could be replaced by multiple two-way valves. Sample discharge mechanism 36 may comprise a two-way valve, piston mechanism or the like. If a piston mechanism is used, then a travel adjustment of the piston could be used to control a size of a respective sample. The piston could be biased with a spring or pressurized fluid. The piston mechanism may be utilized when a pressurized sample is desired that is directed under pressure from the sampling chamber to a pressurized removable sample container, which might comprise a valve to permit removal and addition of another sample container.

Valve 32 may comprise a three-way valve that opens in the extra position to ambient air to replace the check valve. Valves 32 and 34 and/or mechanism 36 may be replaced by a multiport valve.

The foregoing description of the preferred embodiments of the invention has been presented for purposes of illustration and description only. It is not intended to be exhaustive or to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A sampling system for taking samples from a pipeline, comprising:
    a sample line connectable to said pipeline configured for circulating a pressurized fluid from said pipeline and through said sample line whereupon said pressurized fluid is returned to said pipeline;
    a removable sample container;
    a sampling chamber;
    at least one valve operatively connected to said sample line, said sampling chamber, and said removable sample container;
    a processor comprising programming for operating said at least one valve to allow fluid flow from said sample line to said sampling chamber and then closing said at least one valve with respect to said sample line;
    said processor is operable to operate said at least one valve to provide a flow path from said sampling chamber to said removable sample container;
    a sample discharge mechanism connected to said sampling chamber; and
    said programming is operable to determine how many of said samples to take and when to take said samples for each of said removable sample containers based on variables comprising a batch size.

2. The sampling system of claim 1 comprising said sampling chamber is mounted above said removable sample container whereby said sample discharge mechanism utilizes gravity to induce flow from said sampling chamber to said removable sample container.

3. The sampling system of claim 1 further comprising said programming for said processor is operable to operate said at least one valve a plurality of times to produce a plurality of said samples in said removable sample container.

4. The sampling system of claim 1 further comprising said sample discharge mechanism comprises a valve connected to atmospheric pressure to release a sample into said removable sample container or a piston to urge said sample into said removable sample container.

5. The sampling system of claim 1 further comprising said processor is programmed to perform one or more sample chamber purging cycles that are dumped to a purge outlet prior to allowing said pressurized fluid to drain into said removable sample container.

6. The sampling system of claim 1 further comprising said removable sample container is unpressurized.

7. The sampling system of claim 1 further comprising said processor is programmed to control a plurality of valves configured for directing said respective samples to a plurality of removable sample containers.

8. The sampling system of claim 1, further comprising said at least one valve comprises a first valve operatively connected to said sample line and said sampling chamber, and a second valve operatively connected to said sampling chamber and said removable sample container.

9. The sampling system of claim 8, further comprising said sample discharge mechanism comprises a third valve connected to provide selective communication with ambient air and said sampling chamber so that when said third valve is open gravity flow urges said respective sample to drain from said sampling chamber into said removable sample container.

10. A sampling system for taking samples from a pipeline, comprising:
    a sample line comprising an input connection and an output connection, said sample line being operable for connection to said pipeline to receive pressurized fluid to be sampled from said pipeline and for returning said pressurized fluid to said pipeline;
    a sampling chamber;
    a removable sample container;
    at least one valve operatively connected to said sample line, said sampling chamber, and said removable sample container;
    a sample discharge mechanism connected to said sampling chamber to urge a respective sample from said sampling chamber to said removable sample container;
    a processor operatively connected to said at least one valve to control fluid communication between said sample line and said sampling chamber and to control fluid communication between said sampling chamber and said removable sample container; and
    said processor is programmed to perform one or more sampling chamber purging cycles that are dumped to a purge outlet prior to allowing said sample to drain into said removable sample container.

11. The sampling system of claim 10, wherein said at least one valve comprises a first valve operatively connected to said sample line and said sampling chamber, and a second valve operatively connected to said sampling chamber and said removable sample container.

12. The sampling system of claim 11, wherein said sample discharge mechanism further comprises a third valve connected to provide selective communication with ambient air and said sampling chamber so that when said third valve is opened then said third valve connects said sample chamber to ambient air and said sampling chamber.

13. The sampling system of claim 10, further comprising said at least one valve being connected to said purge outlet.

14. The sampling system of claim 10, further comprising:
    a plurality of valves in fluid communication with said sample line, a plurality of sampling chambers, and a plurality of removable sample containers, said processor being operatively connected to said plurality of valves to sequentially operate said plurality of valves to fill said plurality of removable sample containers.

15. The sampling system of claim 10, further comprising a pump that turns on only when a flow rate through said sample line is below a predetermined flow rate.

16. The sampling system of claim 10, further comprising said processor is operable to adjust a number of samples to take in relationship to a size of said removable sample container and a batch size.

17. A sampling system for taking samples from a pipeline, comprising:
    a sample line comprising an input connection and an output connection, said sample line being operable for connection to said pipeline to receive pressurized fluid to be sampled from said pipeline and for returning said pressurized fluid to said pipeline;
    a sampling chamber;
    a plurality of removable sample containers;
    at least one valve operatively connected to said sample line, said sampling chamber, and said plurality of removable sample containers;

a sample discharge mechanism connected to said sampling chamber to urge a respective sample from said sampling chamber to said plurality of removable sample containers;

a processor operatively connected to said at least one valve to control fluid communication between said sample line and said sampling chamber and to control fluid communication between said sampling chamber and said plurality of removable sample containers; and said processor is programmed to determine how many of said samples to take and when to take said samples for each of said plurality of removable sample containers based on variables comprising a batch size.

* * * * *